United States Patent

Pfrengle et al.

[11] Patent Number: 5,986,135
[45] Date of Patent: Nov. 16, 1999

[54] FUNGICIDAL TRIFLUOROMETHYLALKYLAMINO-TRIAZOLOPYRIMIDINES

[75] Inventors: Waldemar Pfrengle, Seibersbach; Klaus-Juergen Pees, Mainz; Guido Albert, Hackenheim; Paul Carter, Wolfsheim; Annerose Rehnig; Henry Van Tuyl Cotter, both of Ingelheim, all of Germany

[73] Assignee: American Cyanamid Company, Madison, N.J.

[21] Appl. No.: 09/160,894

[22] Filed: Sep. 25, 1998

[51] Int. Cl.[6] .................................................. C07C 209/88
[52] U.S. Cl. ........................................... 564/303; 544/263
[58] Field of Search .............................. 544/263; 564/303

[56] References Cited

U.S. PATENT DOCUMENTS

| | | | |
|---|---|---|---|
| 2,528,267 | 10/1950 | Dearborn et al. | 260/570.8 |
| 5,442,117 | 8/1995 | Stahly et al. | 564/304 |

FOREIGN PATENT DOCUMENTS

| | | |
|---|---|---|
| 0 323 637 | 1/1988 | European Pat. Off. . |
| 0 550 113 | 12/1992 | European Pat. Off. . |

*Primary Examiner*—Richard L. Raymond
*Attorney, Agent, or Firm*—Joseph M. Mazzarese

[57] ABSTRACT

An improved process for the preparation of (S)-1,1,1-trifluoroalkyl-2-amines of formula IIIA,

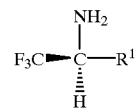

(IIIA)

where $R^1$ is a $C_{1-6}$ alkyl group, from the corresponding racemic mixture, which process includes treating 1 part by mole of the racemic mixture with approximately 0.3 to 0.7 part by mole of D-(−)-tartaric acid in the presence of an inert solvent.

10 Claims, No Drawings

FUNGICIDAL TRIFLUOROMETHYLALKYLAMINO-TRIAZOLOPYRIMIDINES

BACKGROUND OF THE INVENTION

This invention relates to certain triazolopyrimidine compounds, a process for their preparation, compositions containing such compounds, a method for combating a fungus at a locus comprising treating the locus with such compounds and their use as fungicides.

EP-A-0 071 792 claims compounds of the general formula

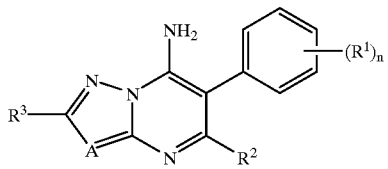

in which $R^1$ represents alkyl, halogen, alkoxy, cyano, cycloalkyl, aryl, aryloxy, arylthio, aralkyl, arylthio, arylalkyl, arylalkyloxy or arylalkylthio each optionally substituted by halogen or alkoxy; or $(R^1)_n$ represents a benzene, indane or tetrahydronaphthalene ring fused with the phenyl ring, aromatic moieties in the above groups being optionally substituted by alkyl, alkoxy, halogen or cyano; n is 1 or 2; $R^2$ and $R^3$ are each hydrogen, alkyl or aryl, A represents a nitrogen atom or a $CR^4$ group, and $R^4$ is as $R^2$ but can also be halogen, cyano or alkoxycarbonyl or together with $R^3$ can form an alkylene chain containing up to two double bonds. The compounds are said to be active against various phytopathogenic fungi, especially those of the phycomycete class. However evidence of fungicidal activity is only provided for these compounds against *Plasmopara viticola*, a member of the oomycete class of fungi.

EP 0 550 113-A2 claims compounds of the general formula

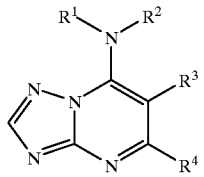

in which $R^1$ represents an optionally substituted alkyl, alkenyl, alkadienyl, cycloalkyl, bicycloalkyl or heterocyclyl group; $R^2$ represents a hydrogen atom or an alkyl group; or $R^1$ and $R^2$ together with the interjacent nitrogen atom represent an optionally substituted heterocyclic ring; $R^3$ represents an optionally substituted aryl group; and $R^4$ represents a hydrogen or halogen atom or a group $-NR^5R^6$ where $R^5$ represents a hydrogen atom or an amino, alkyl, cycloalkyl or bicycloalkyl group and $R^6$ represents a hydrogen atom or an alkyl group. Thus, compounds in which $R^1$ is a trifluoromethylalkyl group are generally embraced by this patent application. However, there is no single compound disclosed in which $R^1$ is an optically enriched trifluoromethylalkyl group.

SUMMARY OF THE INVENTION

The present invention provides a compound of formula I

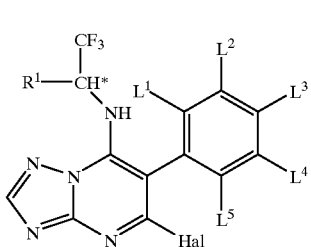

in which
$R^1$ represents a $C_{1-4}$ alkyl group,
CH* indicates a chiral carbon atom,
Hal represents a halogen atom,
$L^1$ through $L^5$ each independently represent an hydrogen or halogen atom or an alkyl, alkoxy or nitro group, characterized in that the enantiomeric excess (ee) of the (S)-enantiomer is at least 70%.

The new compounds show excellent selective fungicidal activity in various crops.

It is an object of the present invention to provide novel, selective fungicidal compounds.

It is another object of the present invention to provide a method for the preparation of the fungicidal compounds of formula I and a method for the resolution of 1,1,1-trifluoroalkyl-2-amines.

It is also an object of the invention to provide methods for controlling undesired fungus by contacting said plants with a fungicidally effective amount of the new compounds.

It is another object of the invention to provide selective fungicidal compositions containing the new compounds as active ingredients.

These and other objects and features of the invention will be more apparent from the detailed description set forth hereinbelow, and from the appended claims.

DETAILED DESCRIPTION OF THE PREFERRED EMBODIMENTS

It has surprisingly been found that the novel optically enriched compounds of formula I

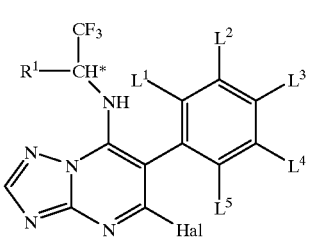

in which $R^1$, Hal and $L^1$ through $L^5$ have the meaning given above having an entantiomeric excess of at least 70% show an excellent fungicidal activity against a broad range of fungi.

In general terms, unless otherwise stated, as used herein the term halogen atom may denote a bromine, iodine, chlorine or fluorine atom, and is especially a bromine, chlorine or fluorine atom.

Hal represents preferably fluorine, chlorine, bromine or iodine, in particular chlorine.

In general terms, unless otherwise stated herein, the terms alkyl, alkoxy as used herein with respect to a radical or moiety refer to a straight or branched chain radical or moiety. As a rule, such radicals have up to 10, in particular up to 6 carbon atoms. Suitably an alkyl moiety has from 1 to 6 carbon atoms, preferably from 1 to 3 carbon atoms. A preferred alkyl moiety is an ethyl or especially a methyl group. Suitably an alkoxy moiety has from 1 to 6 carbon atoms. A preferred alkoxy moiety is a methoxy or ethoxy group.

The invention especially relates to compounds of the general formula I in which any alkyl part of the group $R^1$ which may be straight chained or branched, contains up to 6 carbon atoms, preferably up to 4 carbon atoms, more preferably up to 2 carbon atoms, in particular a methyl group.

Included in the scope of the present invention are the diastereomers caused by atropisomerism of compounds of general formula I, in which the substituents $L^1$ or $L^1$ and $L^2$ are different from $L^5$ or $L^5$ and $L^4$, and the racemates thereof, and salts, N-oxides and acid addition compounds.

The enantiomeric excess of the (S)-enantiomer is at least 70%, preferably more than 75%, in particular at least 80%.

Preferred are compounds of formula I, in which the phenyl group

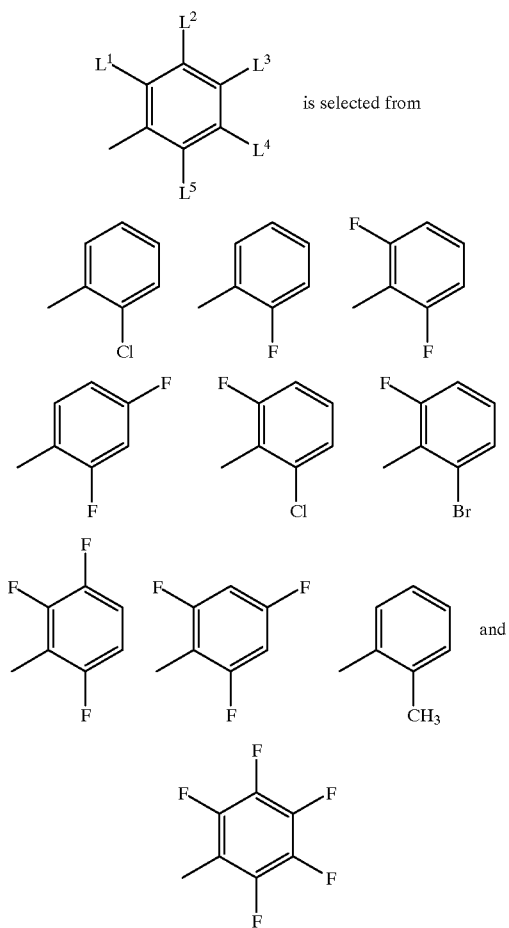

is selected from

The 2,6-difluorophenyl and the 2,4,6-trifluorophenyl group are particularly preferred.

The compounds according to general formula I are oils, gums, or, predominantly crystalline solid materials. They are superior through their valuable fungicidal properties, in particular their enhanced systemicity and enhanced fungicitoxity against rice diseases and powdery mildews. For example, they can be used in agriculture or related fields for the control of phytopathogenic fungi such as *Alternaria solani, Blumeria graminis, Botrytis cinerea, Cercospora beticola, Cladosporium herbarum, Corticium rolfsii, Guignardia bidwellii, Helminthosporium tritici repentis, Leptosphaeria nodorum, Magnaporthe grisea f.* sp. *oryzae, Micronectriella nivalis, Monilinia fructigena, Mycosphaerella fijiensis, Mycosphaerella musicola, Mycosphaerella ligulicola, Mycosphaerella pinodes, Phomopsis viticola, Plasmopara viticola, Podosphaera leucotricha, Pseudopeziza tracheiphila, Phytophthora infestans, Puccinia recondita, Pyrenophora teres, Rhizoctonia solani, Venturia inaequalis, Uncinula necator* and *Sclerotinia sclerotiorum*, in particular for the residual control of *Blumeria graminis, Plasmopara viticola, Puccinia recondita* and *Pyrenophora teres*, and for the curative control of *Puccinia recondite*. The compounds of general formula I according to the invention possess a high fungicidal activity within a wide concentration range and may be used in agriculture without any difficulties.

Moreover, the compounds according to the invention show enhanced residual control of fungi, in particular of grape downy mildew compared with conventional fungicides.

Good results in terms of control of phytopathogenic fungi are obtained with a compound as defined in formula I wherein:

at least one of $L^1$ and $L^5$ represents a halogen atom; and/or
$R^1$ represents a methyl group.

Especially good results in terms of control of phytopathogenic fungi are obtained by using, for example, the following compounds of formula I, wherein the e.e. of the corresponding (S)-enantiomer is at least 80%: 5-chloro-6-(2-chloro-6-fluorophenyl)-7-[2-(1,1,1-trifluoro)propylamino]-[1,2,4]triazolo[1,5-a]pyrimidine, 5-chloro-6-(2,6-difluorophenyl)-7-[2-(1,1,1-trifluoro)propylamino]-[1,2,4]triazolo[1,5-a]pyrimidine, 5-chloro-6-(2,4,6-trifluorophenyl)-7-[2-(1,1,1-trifluoro)propylamino]-[1,2,4]triazolo[1,5-a]pyrimidine, 5-chloro-6-(2-methylphenyl)-7-[2-(1,1,1-trifluoro)propylamino]-[1,2,4]triazolo[1,5-a]pyrimidine, 5-chloro-6-(2-fluorophenyl)-7-[2-(1,1,1-trifluoro)propylamino]-[1,2,4]triazolo[1,5-a]pyrimidine, 5-chloro-6-(2-chlorophenyl)-7-[2-(1,1,1-trifluoro)propylamino]-[1,2,4]triazolo[1,5-a]pyrimidine, 5-chloro-6-(2-bromo-5-chlorophenyl)-7-[2-(1,1,1-trifluoro)propylamino]-[1,2,4]triazolo[1,5-a]pyrimidine, 5-chloro-6-(2-chloro-6-fluorophenyl)-7-[2-(1,1,1-trifluoro)butylaminol]-[1,2,4]triazolo[1,5-a]pyrimidine, 5-chloro-6-(2-fluorophenyl)-7-[2-(1,1,1-trifluoro)butylaminol]-[1,2,4]triazolo[1,5-a]pyrimidine, 5-chloro-6-(2,4,6-trifluorophenyl)-7-[2-(1,1,1-trifluoro)butylamino]-[1,2,4]triazolo[1,5-a]pyrimidine, 5-chloro-6-(2,6-difluorophenyl)-7-[2-(1,1,1-trifluoro)butylamino]-[1,2,4]triazolo[1,5-a]pyrimidine, 5-chloro-6-(2-chlorophenyl)-7-[2-(1,1,1-trifluoro)butylaminol]-[1,2,4]triazolo[1,5-a]pyrimidine, 5-chloro-6-(2,4,6-trifluorophenyl)-7-[2-(1,1,1-trifluoro)-3-methylbutylamino]-[1,2,4]triazolo[1,5-a]pyrimidine, 5-chloro-6-(2,6-difluoro-4-methoxyphenyl)-7-[2-(1,1,1-trifluoro)propylamino]-[1,2,4]triazolo[1,5-a]pyrimidine, 5-chloro-6-(2,4-difluorophenyl)-7-[2-(1,1,1-trifluoro)propylamino]-[1,2,4]triazolo[1,5-a]pyrimidine.

The present invention further provides a process for the preparation of a compound of formula I as defined above which comprises treating a compound of the formula II

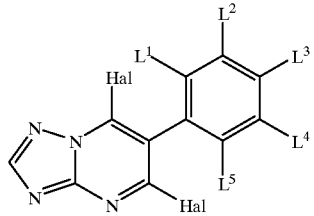
(II)

in which

L$^1$ through L$^5$ and Hal are as defined above, with an optically active amine of the formula III

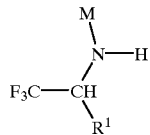
(III)

in which

R$^1$ is as defined above,

M represents a hydrogen atom or a free or complexed metal atom, and the e.e. of the (S)-enantiomer is at least 70%.

The resulting 5,7-dihydroxy-6-phenyltriazolopyrimidines are subsequently treated with a halogenating agent, preferably with a brominating or chlorinating agent, such as phosphorus oxybromide or phosphorus oxychloride, neat or in the presence of a solvent. The reaction is suitably carried out at a temperature in the range from 0° C. to 150° C., the preferred reaction temperature being from 80° C. to 125° C.

The reaction between the 5,7-dihalo-6-phenyltriazolopyrimidines of formula II and the amine or amide of formula III is conveniently carried out in the presence of a solvent. Suitable solvents include ethers, such as dioxane, diethyl ether and, especially, tetrahydrofuran, halogenated hydrocarbons such as dichloromethane and aromatic hydrocarbons, for example toluene. The reaction is suitably carried out at a temperature in the range from 0° C. to 70° C., the preferred reaction temperature being from 10° C. to 35° C. It is also preferred that the reaction is carried out in the presence of a base. Suitable bases include tertiary amines, such as triethylamine, and inorganic bases, such as potassium carbonate or sodium carbonate. Alternatively, an excess of the compound of formula III may serve as a base.

Compounds of formula II are known e.g. from EP 0 550 113 and are conventionally prepared by reacting 3-amino-1,2,4-triazole with 2-phenyl-substituted malonic acid ester of formula IV,

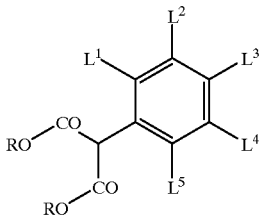
(IV)

wherein R represents alkyl, under alkaline conditions, preferably using high boiling tertiary amines as for example tri-n-butylamine.

The chiral amines of formula III, wherein M represents a hydrogen atom, are known in the literature or commercially available or may be prepared analogously to methods that are known per se. For example, they may be prepared from the corresponding chiral amino acids with fluorination agents such as sulfurtetrafluoride/HF (e.g. EP 0 323 637).

Furthermore, they may be prepared from the corresponding trifluoromethyl ketones by reaction with chiral α-phenylethylamine, treatment of the resulting chiral ketimines with a base, in particular DBU, and hydrolysis with mineral acid (e.g. V. A. Soloshonok, T. Ono, J. Org. Chem. 1997, 62, 3030–3031).

In a preferred embodiment of the present invention the chiral amines of formula III are prepared from the corresponding racemic amines by conversion to diastereomeric salt with a chiral organic acid such as tartaric acid and fractional crystallisation of the diastereomeric salt.

The invention relates to an improved process for the preparation of (S)-1,1,1-trifluoroalkyl-2-amine of formula IIIA

(IIIA)

wherein R$^1$ has the meaning given, by resolution of the corresponding racemic mixture of 1,1,1-trifluoroalkyl-2-amine with optically active tartaric acid, wherein 1 mole of the racemic mixture of 1,1,1-trifluoroalkyl-2-amine is treated with 0.3 to 0.7 mole of D-(−)-tartaric acid in the presence of an inert solvent.

Further preferred embodiments of the process according to the present invention is a process wherein:

- diastereomeric salt formed from the (S)-1,1,1-trifluoroalkyl-2-amine and D-(−)-tartaric acid precipitates from the solution;
- 1 mole of the racemic mixture of 1,1,1-trifluoroalkyl-2-amine is treated with about 0.5 mole of D-(−)-tartaric acid;
- the diastereomeric salt is separated by filtration techniques;
- the diastereomeric salt is treated with a strong base to liberate the optically active amine from the tartaric acid;
- the inert solvent is water or an alcohol or a mixture thereof;

the 1,1,1-trifluoroalkyl-2-amine is 1,1,1-trifluoropropyl-2-amine (S)-1,1,1-trifluoropropyl-2-amine obtained is treated with hydrochloric acid and the resulting the hydrochloride has a specific rotation [α] of -4.26 at a wavelength of 589 nm at 27° C.;

the resulting (S)-1,1,1-trifluoroalkyl-2-amine has an enantiomeric excess of at least 70%, preferably at least 80%.

The obtained (R)-1,1,1-trifluoroalkyl-2-amine can be easily recycled for example according to one of the following reaction sequences:

Racemization 1:

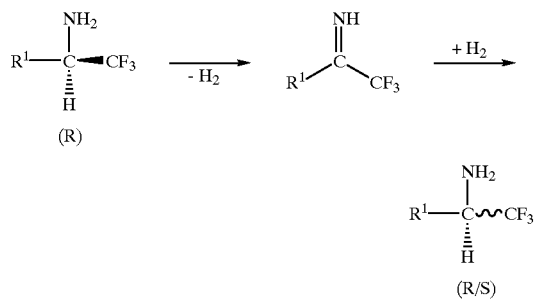

Racemization 2:

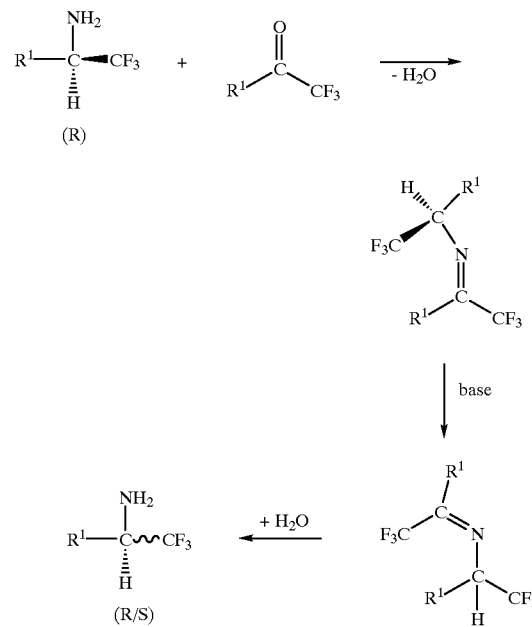

Due to excellent activity, the compounds of formula I may be used in cultivation of all plants where infection by phytopathogenic fungi is not desired, e.g. cereals, solanaceous crops, vegetables, legumes, apples, vine.

The invention further provides a fungicidal composition which comprises an active ingredient, which is at least one compound of formula I as defined above, and one or more carriers. A method of making such a composition is also provided which comprises bringing a compound of formula I as defined above into association with the carrier(s). Such a composition may contain a single active ingredient or a mixture of several active ingredients of the present invention. It is also envisaged that different isomers or mixtures of isomers may have different levels or spectra of activity and thus compositions may comprise individual isomers or mixtures of isomers.

A composition according to the invention preferably contains from 0.5% to 95% by weight (w/w) of active ingredient(s).

A carrier in a composition according to the invention is any material with which the active ingredient is formulated to facilitate application to the locus to be treated (which locus may be, for example, a plant, seed, soil, or water in which a plant grows), or to facilitate storage, transport or handling. A carrier may be a solid or a liquid, including material which is normally a gas but which has been compressed to form a liquid.

The compositions may be manufactured into e.g. emulsion or emulsifiable concentrates, solutions, oil in water emulsions, wettable powders, soluble powders, suspension concentrates, dusts, granules, water dispersible granules, aerosols, micro-capsules, gels, tablets and other formulation types by well-established procedures. These procedures include intensive mixing and/or milling of the active ingredients with other substances, such as fillers, solvents, solid carriers, surface active compounds (surfactants), and optionally solid and/or liquid auxiliaries and/or adjuvants. The form of application such as spraying, atomizing, dispersing or pouring may be chosen like the compositions according to the desired objectives and the given circumstances.

Solvents may be aromatic hydrocarbons, e.g. Solvesso® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or γ-butyrolactone, higher alkyl pyrrolidones, e.g. n-octylpyrrolidone or cyclohexylpyrrolidone, epoxidized plant oil esters, e.g. methylated coconut or soybean oil ester and water. Mixtures of different liquids are often suitable.

Solid carriers, which may be used for dusts, wettable powders, water dispersible granules, or granules, may be mineral fillers, such as calcite, talc, kaolin, montmorillonite or attapulgite. The physical properties may be improved by addition of highly dispersed silica gel or polymers. Carriers for granules may be porous material, e.g. pumice, kaolin, sepiolite, bentonite; non-sorptive carriers may be calcite or sand. Additionally, a multitude of pre-granulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

Surfactants may be nonionic, anionic, cationic or zwitterionic substances with good dispersing, emulsifying and wetting properties depending on the nature of the compound according to general formula I to be formulated. Surfactants may also mean mixtures of individual surfactants.

Wettable powders of this invention suitably contain 5 to 90% w/w of active ingredient, and in addition to solid inert carrier, 3 to 10% w/w of dispersing and wetting agents and, where necessary, 0 to 10% w/w of stabilizer(s) and/or other additives such as penetrants or stickers. Dusts may be formulated as a dust concentrate having a similar composition to that of a wettable powder but without a dispersant, and may be diluted in the field with further solid carrier to give a composition usually containing 0.5 to 10% w/w of active ingredient. Water dispersible granules and granules of this invention typically have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents. Emulsifiable concentrates may contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates are suitably milled so as to obtain a stable, non-sedimenting flowable product and preferably contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation and crystalization, or as antifreeze agents.

Aqueous dispersions and emulsions, for example compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected.

The biological activity of the active ingredient can also be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient.

As a commodity, the compositions preferably may be in a concentrated form, whereas the end user generally employs diluted compositions. The compositions may be diluted to a concentration down to 0.001% of active ingredient. The doses usually are in the range from 0.01 to 10 kg a.i./ha.

Examples of formulations according to the invention are:

Emulsion Concentrate (EC)

| Active Ingredient | Compound of Example 2 | 30% (w/v) |
|---|---|---|
| Emulsifier(s) | Atlox ® 4856 B/Atlox ® 4858 B [1] (mixture containing calcium alkyl aryl sulfonate, fatty alcohol ethoxylates and light aromatics/ mixture containing calcium alkyl aryl sulfonate, fatty alcohol ethoxylates and light aromatics) | 5% (w/v) |
| Solvent | Shellsol ® A [2] (mixture of $C_9$–$C_{10}$ aromatic hydrocarbons) | to 1000 ml |

Suspension Concentrate (SC)

| Active Ingredient | Compound of Example 2 | 50% (w/v) |
|---|---|---|
| Dispersing agent | Soprophor ® FL [3] (polyoxyethylene polyaryl phenyl ether phosphate amine salt) | 3% (w/v) |
| Antifoaming agent | Rhodorsil ® 422 [3] (nonionic aqueous emulsion of polydimethylsiloxanes) | 0.2% (w/v) |

-continued

| Structure agent | Kelzan ® S [4] (Xanthan gum) | 0.2% (w/v) |
|---|---|---|
| Antifreezing agent | Propylene glycol | 5% (w/v) |
| Biocidal agent | Proxel ® 5) (aqueous dipropylene glycol solution containing 20% 1,2-benisothia-zolin-3-one) | 0.1% (w/v) |
| Water | | to 1000 ml |

Wettable Powder (WP)

| Active Ingredient | Compound of Example 2 | 60% (w/w) |
|---|---|---|
| Wetting agent | Atlox ® 4995 [1] (polyoxyethylene alkyl ether) | 2% (w/w) |
| Dispersing agent | Witcosperse ® D-60 [6] (mixture of sodium salts of condensed naphthalene sulfonic acid and alkylarylpolyoxy acetates) | 3% (w/w) |
| Carrier I Filler | Kaolin | 35% (w/w) |

Water Dispersible Granules (WG)

| Active Ingredient | Compound of Example 2 | 50% (w/w) |
|---|---|---|
| Dispersing/ Binding agent | Witcosperse ® D450 [6] (mixture of sodium salts of condensed naphthalene sulfonic acid and alkyl sulfonates) | 8% (w/w) |
| Wetting agent | Morwet ® EFW [6] (formaldehyde condensation product) | 2% (w/w) |
| Antifoaming agent | Rhodorsil ® EP 6703 [3] (encapsulated silicone) | 1% (w/w) |
| Disintegrant | Agrimer ® ATF [7] (cross-linked homopolymer of N-vinyl-2-pyrrolidone) | 2% (w/w) |
| Carrier I Filler | Kaolin | 35% (w/w) |

[1] commercially available from ICI Surfactants
[2] commercially available from Deutsche Shell AG
[3] commercially available from Rhone-Poulenc
[4] commercially available from Kelco Co.
[5] commercially available from Zeneca
[6] commercially available from Witco
[7] commercially available from International Speciality Products The compositions of this invention can also comprise other compounds having biological activity, e.g. compounds having similar or complementary pesticidal activity or compounds having plant growth regulating, fungicidal or insecticidal activity. These mixtures of pesticides can have a broader spectrum of activity than the compound of formula I alone. Furthermore, the other pesticide can have a synergistic effect on the pesticidal activity of the compound of formula I.

The other fungicidal compound can be, for example, one which is also capable of combating diseases of cereals (e.g. wheat) such as those caused by Erysipha, Puccinia, Septoria, Gibberella and Helminthosporium spp., seed and soil borne diseases and downy and powdery mildews on vines, early and late blight on solanaceous crops, and powdery mildew and scab on apples etc. These mixtures of fungicides can have a broader spectrum of activity than the compound of formula I alone. Furthermore, the other fungicide can have a synergistic effect on the fungicidal activities of the compound of formula I.

Examples of the other fungicidal compounds are anilazine, azoxystrobin, benalaxyl, benomyl, bethoxazin, binapacryl, bitertanol, blasticidin S, Bordeaux mixture, bromuconazole, bupirimate, captafol, captan, carbendazim, carboxin, carpropamid, chlorbenzthiazon, chlorothalonil, chlozolinate, copper-containing compounds such as copper oxychloride, and copper sulfate, cycloheximide, cymoxanil, cypofuram, cyproconazole, cyprodinil, dichlofluanid, dichlone, dichloran, diclobutrazol, diclocymet, diclomezine, diethofencarb, difenoconazole, diflumetorim, dimethirimol, dimethomorph, diniconazole, dinocap, ditalimfos, dithianon, dodemorph, dodine, edifenphos, epoxiconazole, etaconazole, ethirimol, etridiazole, famoxadone, fenapanil, fenarimol, fenbuconazole, fenfuram, fenhexamid, fenpiclonil, fenpropidin, fenpropimorph, fentin, fentin acetate, fentin hydroxide, ferimzone, fluazinam, fludioxonil, flumetover, fluquinconazole, flusilazole, flusulfamide, flutolanil, flutriafol, folpet, fosetyl-aluminium, fuberidazole, furalaxyl, furametpyr, guazatine, hexaconazole, imazalil, iminoctadine, ipconazole, iprodione, isoprothiolane, kasugamycin, kitazin P, kresoxim-methyl, mancozeb, maneb, mepanipyrim, mepronil, metalaxyl, metconazole, methfuroxam, myclobutanil, neoasozin, nickel dimethyldithiocarbamate, nitrothalisopropyl, nuarimol, ofurace, organo mercury compounds, oxadixyl, oxycarboxin, penconazole, pencycuron, phenazineoxide, phthalide, polyoxin D, polyram, probenazole, prochloraz, procymidione, propamocarb, propiconazole, propineb, pyrazophos, pyrifenox, pyrimethanil, pyroquilon, pyroxyfur, quinomethionate, quinoxyfen, quintozene, spiroxamine, SSF-126, SSF-129, streptomycin, sulfur, tebuconazole, tecloftalame, tecnazene, tetraconazole, thiabendazole, thifluzamide, thiophanate-methyl, thiram, tolclofosmethyl, tolylfluanid, triadimefon, triadimenol, triazbutil, triazoxide, tricyclazole, tridemorph, triflumizole, triforine, triticonazole, validamycin A, vinclozolin, XRD-563, zarilamid, zineb, and ziram.

In addition, the formulations according to the invention may contain at least one compound of formula I and any of the following classes of biological control agents such as viruses, bacteria, nematodes, fungi, and other microorganisms which are suitable to control insects, weeds or plant diseases or to induce host resistance in the plants. Examples of such biological control agents are: *Bacillus thuringiensis, Verticillium lecanii, Autographica californica NPV, Beauvaria bassiana, Ampelomyces quisqualis, Bacilis subtilis, Pseudomonas chlororaphis, Pseudomonas fluorescens, Steptomyces griseoviridis* and *Trichoderma harzianum*.

Moreover, the formulations according to the invention may contain at least one compound of formula I and a chemical agent that induces the systemic acquired resistance in plants such as for example nicotinic acid or derivatives thereof, 2,2-dichloro-3,3-dimethylcyclopropylcarboxylic acid or BION.

The compounds of formula I can be mixed with soil, peat or other rooting media for the protection of the plants against seed-borne, soil-borne or foliar fungal diseases.

The invention also includes the fungicidal use of a compound of formula I as defined above or a composition as defined above, and a method for combating fungus at a locus, which comprises treating the locus (which may be, for example, plants subject to or subjected to fungal attack, seeds of such plants or the medium in which such plants are growing or are to be grown), with such a compound or composition.

The present invention is of wide applicability in the protection of crop and ornamental plants against fungal attack. Typical crops which may be protected include vines, grain crops such as wheat and barley, rice, sugar beet, top fruit, peanuts, potatoes, vegetables and tomatoes. The duration of the protection is normally dependent on the individual compound selected, and also a variety of external factors, such as climate, whose impact is normally mitigated by the use of a suitable formulation.

The following examples further illustrate the present invention. It should be understood, however, that the invention is not limited solely to the particular examples given below.

EXAMPLE 1

Resolution of 1,1,1-trifluoroprop-2-ylamine

To D(–)-tataric acid (25.5 g, 0.17 mol) in methanol (250 ml) is added racemic trifluoroisopropyl amine (38 g, 0.34 mol) as a methanolic solution (100 ml). After the addition of half of the amine a white precipitate forms. After the addition is complete the mixture is briefly heated to reflux. It is then allowed to cool to ambient. The mixture is cooled in an ice bath and the salt is isolated by filtration and dried in vacuo. The obtained product (36 g) is then recrystallized from boiling methanol (170 ml) to yield 29.0 g of the salt which is finally recrystallized from 140 ml methanol to furnish a final yield of 25.5 g (S)-trifluoroisopropyl amine D(–)-tartrate.

For the preparation of the target compound the amine is then liberated from the salt by placing the salt in a distillation apparatus and carefully adding aqueous 50% sodium hydroxide with heating and stirring.

Liberation of the D(–)-tartrate gives rise to an amine with a negative optical rotation: $[a]_D^{27}$: –3.67 (c=10, methanol).

It is noteworthy that the optical rotation inverts for the hydrochlorides. $[a]_D^{27}$: +4.26(c=10, methanol).

Determination of the Enantomeric Purity

In a small vial approx. 7 mg of the tartrate is dissolved in 0.6 ml $CDCl_3$. Aqueous sodium hydroxide (50%, 3 drops) is added and the two phase mixture is shaken vigorously for 10 seconds. The organic layer is then separated via a pasteur pipette and filtered through a small plug of cotton directly into the NMR-tube. (S)-(+)-1-(9-anthryl)-2,2,2-trifluoro ethanol (21 mg) is added and the $^1$H-NMR spectrum (400 MHz) is recorded. The ratio of the enantiomers is determined by integration of the signals of the methyl group at 1.20 ppm (R-enantiomer) and 1.17 ppm (S-enantiomer). The enantiomeric excess of the S-enantiomer is >85%

EXAMPLE 2

5-Chloro-6-(2,4,6-trifluorophenyl)-7-N-[(S)-(1,1,1-trifluoroprop-2-ylamino)]-1,2,4-triazolo[1.5a] pyrimidine A mixture of (S)-1,1,1-trifluoroprop-2-ylamine (4.2 mmoles) obtained according to example 1 and dichloromethane (10 ml) is added to a mixture of 5,7-dichloro-6-(2,4,6-trifluorophenyl)-1,2,4-triazolo[1.5a]pyrimidine (1.4 mmoles, obtained from diethyl 2,4,6-trifluorophenylmalonate and 3-amino-1,2,4-triazole as described in EP 0 770 615) and dichloromethane (30 ml) under stirring. The reaction mixture is stirred 16 hours at room temperature, subsequently washed two times with 1 N hydrochloric acid and once with water. The organic layer is separated, dried with anhydrous sodium sulfate and the solvent is evaporated under reduced pressure. Treatment of the resulting light brown oil with tert.-butyl methyl ether (50 ml) yields beige crystals having a melting point of 117–121° C. and an enantiomeric excess of >98%.

EXAMPLES 3–16

The following examples (Table I; structure and melting point) are synthesized analogously to Examples 1 and 2.

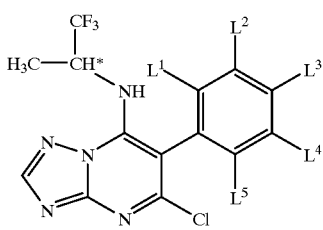

(CH* indicates that the compound has an enantiomeric excess of at least 80% with respect to the (S)-isomer)

| Example | L¹ | L² | L³ | L⁴ | L⁵ | |
|---------|-----|-----|------|-----|-----|-----------|
| 3 | Cl | H | H | H | H | |
| 4 | F | H | H | H | H | |
| 5 | F | H | H | H | F | m.p. 167° C. |
| 6 | Cl | H | H | H | F | |
| 7 | CH₃ | H | H | H | H | |
| 8 | Br | H | H | Cl | H | |
| 9 | H | H | Cl | H | H | |
| 10 | H | H | Br | H | H | |
| 11 | H | H | OCH₃ | H | H | |
| 12 | H | H | NO₂ | H | H | |
| 13 | F | H | OCH₃ | H | F | |
| 14 | F | H | H | H | Br | |
| 15 | F | F | H | H | F | |
| 16 | F | H | F | H | H | |

Biological Investigations

A. Determination of Minimum Inhibitory Concentration by Test Compounds in the Serial Dilution Test with Various Phytopathogenic Fungi The MIC (Minimum Inhibitory Concentration) value, which indicates the lowest concentration of the active ingredient in the growth medium which causes a total inhibition of myecelial growth, is determined by serial dilution tests using Microtiter plates with 24 or 48 wells per plate. The dilution of the test compounds in the nutrient solution and the distribution to the wells is carried out by a TECAN RSP 5000 Robotic Sample Processor. The following test compound concentrations are used: 0.05, 0.10, 0.20, 0.39, 0.78, 1.56, 3.13, 6.25, 12.50, 25.00, 50.00 and 100.00 μg/ml. For preparation of the nutrient solution, V8 vegetable juice (333 ml) is mixed with calcium carbonate (4.95 g), centrifuged, the supernatant (200 ml) diluted with water (800 ml) and autoclaved at 121° C. for 30 min.

The respective inocula (*Alternaria solani*, ALTESO; *Botrytis cinerea*, BOTRCI; *Guignardia bidwellii*, GUIGBI, *Leptosphaeria nodorum*, LEPTNO; *Phytophthora infestans*, PHYTIN; *Magnaporthe grisea f.* sp. *oryzae*, PYRIOR; *Pyrenophora teres*, PYRNTE; *Phomopsis viticola*, PHOPVI, *Pseudopeziza tracheiphila*, PSEUTR, *Rhizoctonia solani*, RHIZSO;) are added into the wells as spore suspensions (50 ml; 5×10⁵/ml) or agar slices (6 mm) of an agar culture of the fungus.

After 6–12 days incubation at suitable temperatures (18–25° C.), the MIC values are determined by visual inspection of the plates.

TABLE II

Minimum Inhibitory Concentration of Compound of Example 2 against different pathogens

| PATHOGEN | Example 1 S-Isomer | Comparison (R/S)-Racemate |
|----------|--------------------|-----------------------------|
| ALTESO | 0.39 | 1.56 |
| BOTRCI | 1.56 | 3.13 |
| GUIGBI | <0.05 | 0.1 |
| LEPTNO | 0.1 | 0.78 |
| PHYTIN | 25 | >100 |
| PYRIOR | 0.2 | 0.78 |
| PYRNTE | 3.13 | 6.25 |
| PHOPVI | 0.39 | 0.78 |
| PSEUTR fs 130 | <0.05 | <0.05 |
| RHIZSO | 1.56 | 3.13 |

Besides Botrytis cinerea the targets included 3 other grape pathogens which occur early in the grape growing season: *Guignardia bidwellii* (black rot), *Phomopsis viticola* (dead arm) and *Pseudopeziza tracheiphila* (Red fire disease). The results indicate that both the (R/S)-racemate and the two (S)-enantiomer have good to very good activity against these grape fungi. However, the activity of the (S)-isomer is more than twice as high against almost all pathogens.

B. Determination of the Efficacy of Test Compounds in Greenhouse Trials

The efficacy of the (R/S)-racemate and the (S)-enantiomer was also investigated in-vivo in greenhouse trials against several cereal diseases and diseases of dicotyledonous crops. The curative and residual activity as well as the systemicity of both the compounds was assessed.

Both showed fungicidal activity against the diseases tested (Tables III and IV). In all tests, the (S)-enatiomer performed comparable to the racemate, however in most tests it was even better.

TABLE III

Efficacy (in % disease control) of Compound of Example 2 ((S)-enantiomer) against wheat leaf rust (WLR), and wheat powdery mildew (WPM) (curatively (2 dc) and residually (2dp) after foliar application) compared with the corresponding (R/S)-racemate

| | WLR 2 dc | | | | WLR 2 dp | | | WPM 2dp | | |
|---|---|---|---|---|---|---|---|---|---|---|
| | rate (ppm) | | | | | | | | | |
| Compound | 25 | 6.3 | 1.6 | 0.4 | 25 | 6.3 | 1.6 | 25 | 6.3 | 1.6 |
| Example 2 (S)-enantiomer | 100 | 100 | 100 | 90 | 100 | 100 | 0 | 100 | 81 | 0 |
| Comparison (R/S)-racemate | 100 | 100 | 100 | 59 | 100 | 95 | 0 | 100 | 92 | 0 |

TABLE IV

Efficacy (in % disease control) of Compound of Example 2 ((S)-enantiomer), against apple scab (AS) and (after foliar application curatively two days after the inoculation (2 d c) or prophylactically two or three days before the inoculation (2 d p) compared with the corresponding (R/S)-racemate

|  | AS 2 dc | | | AS 2 dp | | |
|---|---|---|---|---|---|---|
|  | rate (ppm) | | | | | |
| Compound | 6.3 | 1.6 | 0.4 | 6.3 | 1.6 | 0.4 |
| Example 1 (S)-Enantiomer | 100 | 78 | 30 | 98 | 92 | 63 |
| Comparison (R/S)-Racemate | 77 | 67 | 3 | 95 | 59 | 56 |

TABLE V

Efficacy (in % disease control) of Compound of Example 5 ((S)-enantiomer) against grape downy mildew (GDM), wheat leaf rust (WLR), wheat powdery mildew (WPM) barley net blotch (BNB) (residually (1 d p) after foliar application) compared with the corresponding (R/S)-racemate

|  | GDM | | | WLR | | | WPM | | | BNB | | |
|---|---|---|---|---|---|---|---|---|---|---|---|---|
|  | rate (ppm) | | | | | | | | | | | |
| Compound | 20 | 4 | 0.8 | 20 | 4 | 0.8 | 20 | 4 | 0.8 | 20 | 4 | 0.8 |
| Example 5 (S)-enantiomer | 89 | 40 | 1 | 100 | 99 | 91 | 100 | 68 | 14 | 85 | 17 | 23 |
| Comparison (R/S)-racemate | 81 | 34 | 23 | 100 | 87 | 68 | 98 | 27 | 7 | 58 | 0 | 1 |

TABLE IV

Efficacy (in % disease control) of Compound of Example 5 ((S)-enantiomer) against wheat leaf rust (WLR) (curatively (2 d c) after foliar application) compared with the corresponding (R/S)-racemate

|  | WLR | | |
|---|---|---|---|
|  | rate (ppm) | | |
| Compound | 20 | 4 | 0.8 |
| Example 5 (S)-enantiomer | 100 | 84 | 20 |
| Comparison (R/S)-racemate | 99 | 5 | 0 |

What is claimed is:

1. An improved process for the preparation of (S)-1,1,1-trifluoroalkyl-2-amines of formula IIIA,

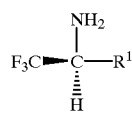

(IIIA)

wherein $R^1$ represents a $C_{1-6}$ alkyl group, from the corresponding racemic mixture of 1,1,1-trifluoroalkyl-2-amine, the improved process comprising treating 1 part by mole of said racemic mixture with approximately 0.3 to 0.7 part by mole of D-(−)-tartaric acid in the presence of an inert solvent to form a diastereomeric salt.

2. The process according to claim 1 wherein the diastereomeric salt precipitates out of said inert solvent.

3. The process according to claim 1 wherein 1 part by mole of said racemic mixture is treated with about 0.5 part by mole of (D)-(−)-tartaric acid.

4. The process according to claim 2 further comprising separating said precipitate from said inert solvent by filtration.

5. The process according to claim 1 further comprising treating said diastereomeic salt with a strong base to liberate the optically active amine of formula IIIA.

6. The process according to claim 1 wherein said inert solvent is water, an alcohol, or a mixture thereof.

7. The process according to claim 1 wherein said 1,1,1-trifluoroalkyl-2-amine is 1,1,1-trifluoropropyl-2-amine.

8. The process according to claim 7 further comprising treating the (S)-1,1,1-trifluoropropyl-2-amine with hydrochloric acid to obtain a hydrochloride having a specific rotation of -4.26 at a wavelength of 589 nm at 27° C.

9. The process according to claim 1 wherein the resulting (S)-1,1,1-trifluoroalkyl-2-amine has an enantiomeric excess of at least 70%.

10. The process according to claim 9 wherein said enantiomeric excess is at least 80%.

* * * * *